US006645234B2

(12) United States Patent
Evans et al.

(10) Patent No.: US 6,645,234 B2
(45) Date of Patent: Nov. 11, 2003

(54) CARDIOVASCULAR GUIDING CATHETER WITH HEAT EXCHANGE PROPERTIES AND METHODS OF USE

(75) Inventors: Scott M. Evans, Santa Ana, CA (US); Blair D. Walker, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 10/061,488

(22) Filed: Feb. 1, 2002

(65) Prior Publication Data

US 2002/0120314 A1 Aug. 29, 2002

Related U.S. Application Data

(63) Continuation-in-part of application No. 09/503,014, filed on Feb. 11, 2000, now Pat. No. 6,409,747, which is a continuation of application No. 09/063,984, filed on Apr. 21, 1998, now Pat. No. 6,126,684, application No. 10/061,488, which is a continuation-in-part of application No. 09/565,039, filed on May 3, 2000, now Pat. No. 6,432,124, which is a continuation of application No. 09/375,079, filed on Aug. 16, 1999, now Pat. No. 6,149,670, which is a continuation-in-part of application No. 09/266,452, filed on Mar. 11, 1999, now Pat. No. 6,458,150, which is a continuation-in-part of application No. 09/253,109, filed on Feb. 19, 1999, now abandoned, which is a continuation-in-part of application No. 09/063,984, filed on Apr. 21, 1998, now Pat. No. 6,126,684.

(51) Int. Cl.[7] ................................................. A61F 7/00
(52) U.S. Cl. ...................... 607/105; 607/106; 607/113
(58) Field of Search ...................... 606/20–23, 27, 606/28; 607/96, 98, 99, 104–106, 113

(56) References Cited

U.S. PATENT DOCUMENTS 4,425,919 A * 1/1984 Alston et al. ............... 600/435

| 5,306,252 | A | * | 4/1994 | Yutori et al. | 600/585 |
|---|---|---|---|---|---|
| 5,591,142 | A | * | 1/1997 | Van Erp | 604/526 |
| 5,837,003 | A | | 11/1998 | Ginsburg | 607/106 |
| 5,868,735 | A | * | 2/1999 | Lafontaine | 606/21 |
| 6,033,383 | A | * | 3/2000 | Ginsburg | 604/113 |
| 6,110,168 | A | | 8/2000 | Ginsburg | 606/27 |
| 6,126,684 | A | | 10/2000 | Gobin et al. | |
| 6,149,670 | A | | 11/2000 | Worthen et al. | |
| 6,149,676 | A | | 11/2000 | Ginsburg | 607/106 |
| 6,231,594 | B1 | | 5/2001 | Dae | 607/96 |
| 6,393,320 | B2 | | 5/2002 | Lasersohn et al. | |
| 6,432,124 | B1 | | 8/2002 | Worthen | 607/105 |
| 6,527,798 | B2 | | 3/2003 | Ginsburg | 607/106 |
| 2001/0005791 | A1 | | 6/2001 | Ginsburg | 607/106 |
| 2001/0044644 | A1 | | 11/2001 | Keller et al. | 607/105 |
| 2002/0045925 | A1 | | 4/2002 | Keller et al | 607/106 |
| 2002/0111616 | A1 | | 8/2002 | Dea et al. | 606/41 |

OTHER PUBLICATIONS

U.S. patent application Ser. No. 09/477,490, Lasersohn et al., pending.

(List continued on next page.)

Primary Examiner—Roy D. Gibson
(74) Attorney, Agent, or Firm—John L. Rogitz

(57) ABSTRACT

An intravenous cardiovascular guiding catheter system (apparatus and method) for controlling patient temperature includes a generally tubular elongate body having a guide lumen with a guide duct disposed at the distal tip of the catheter for providing a pathway through which medical apparatus may be advanced in the patient's circulatory system. The catheter also comprises one or more lumens for conveying a heat exchange fluid to one or more heat exchange elements that exchange heat with the patient's blood to control the patient's temperature. The catheter may have an internal heating element that heats or cools the heat exchange fluid. The catheter also preferably has one or more infusion lumens for providing access to the patient's central blood supply. The catheter may be used to treat myocardial infarction.

25 Claims, 3 Drawing Sheets

OTHER PUBLICATIONS

U.S. patent application Ser. No. 09/540,693, Worthen et al., pending.
U.S. patent application Ser. No. 09/822,984, Worthen et al., pending.
U.S. patent application Ser. No. 09/911,369, Lasersohn et al., pending.
U.S. patent application Ser. No. 09/911,370, Lasersohn et al., pending.
U.S. patent application Ser. No. 10/015,505, Tzeng et al., pending.
U.S. patent application Ser. No. 10/100,555, Worthen et al., pending.
U.S. patent application Ser. No. 10/057,334, Aliberto et al., pending.
U.S. patent application Ser. No. 09/253,109, Evans et al., pending.
U.S. patent application Ser. No. 09/266,452, Evans et al., pending.
U.S. patent application Ser. No. 09/503,074, Gobin et al., pending.
U.S. patent application Ser. No. 09/565,039, Worthen et al., pending.
Novel Reperfusion Technologies: Adjunctive Devices Come of Age, Medtech Insight–Interventional, Jan. 2002, pp. 310–313.

* cited by examiner

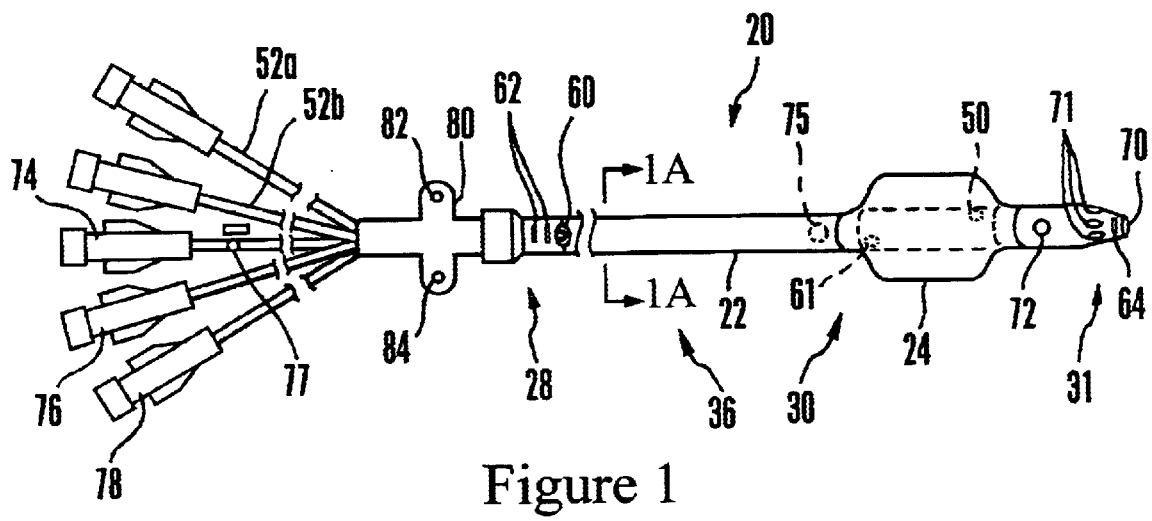
Figure 1
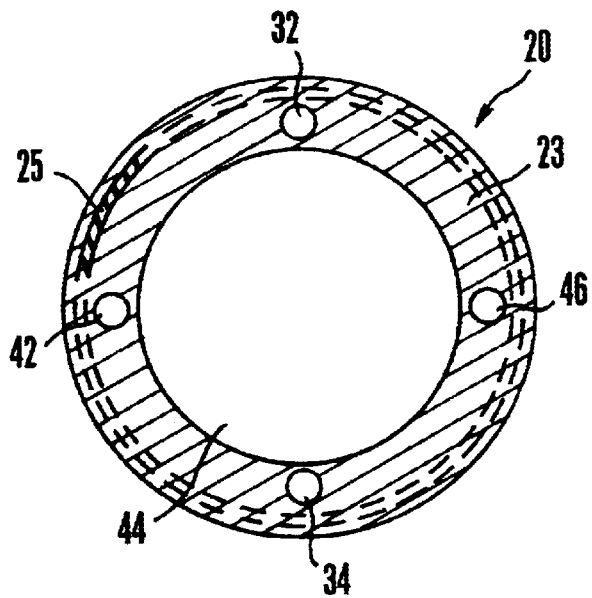
Figure 1A

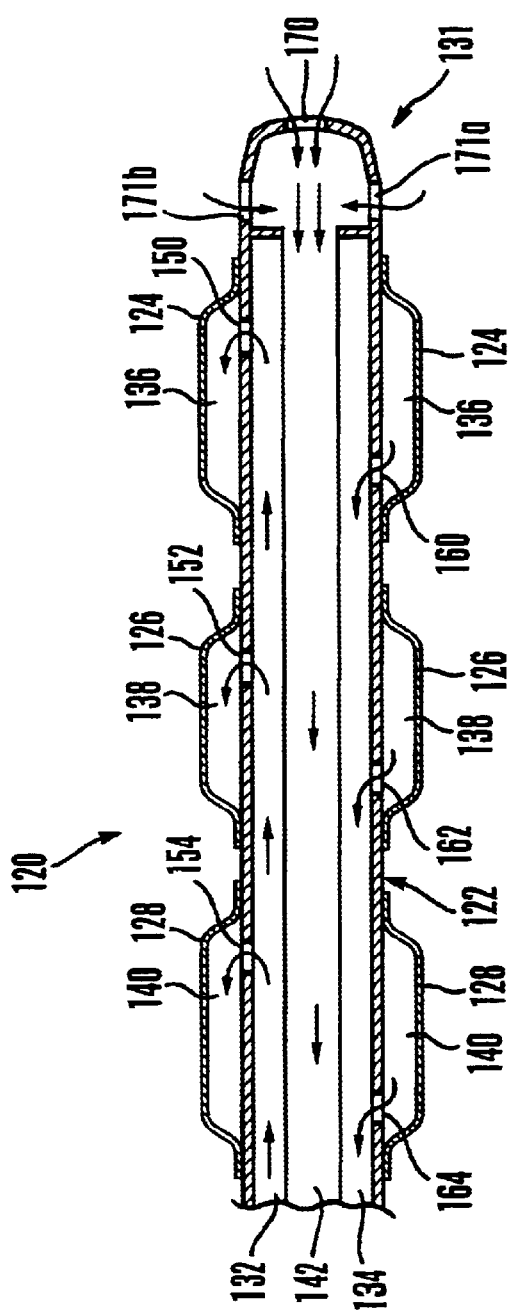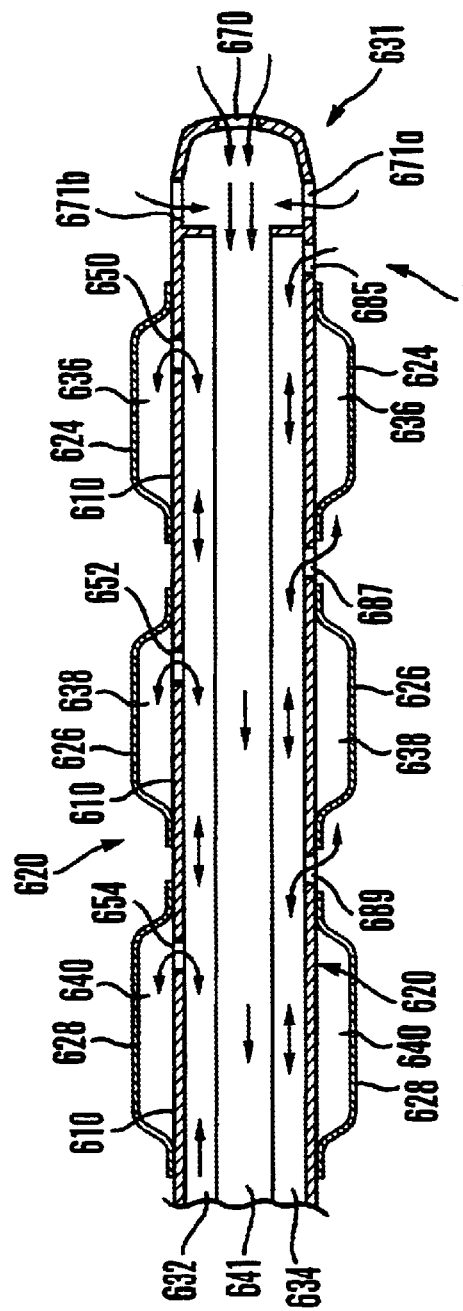

CARDIOVASCULAR GUIDING CATHETER WITH HEAT EXCHANGE PROPERTIES AND METHODS OF USE

CROSS REFERENCE TO RELATED APPLICATIONS

This application is a continuation-in-part of U.S. patent application Ser. No. 09/503,014 filed on Feb. 11, 2000, now U.S. Pat. No. 6,409,747, which is a continuation of U.S. patent application Ser. No. 09/063,984 filed on Apr. 21, 1998, now issued as U.S. Pat. No. 6,126,684, the disclosures of which are herein incorporated by reference in their entirety; and further, the present application is a continuation-in-part of U.S. patent application Ser. No. 09/565,039 filed on May 3, 2000, now U.S. Pat. No. 6,432,124, which is a continuation of U.S. patent application Ser. No. 09/375,079 filed on Aug. 16, 1999, now issued as U.S. Pat. No. 6,149,670, which is a continuation-in-part of U.S. patent application Ser. No. 09/266,452 filed on Mar. 11, 1999 now U.S. Pat. No. 6,458,150, which is a continuation-in-part of U.S. patent application Ser. No. 09/253,109 filed on Feb. 19, 1999, now abandoned, which is a continuation-in-part of U.S. patent application Ser. No. 09/063,984 filed on Apr. 21, 1998, now issued as U.S. Pat. No. 6,126,684, the disclosures of which are herein incorporated by reference in their entirety.

BACKGROUND OF THE INVENTION

The field of the present invention is apparatus and methods for providing access to a patient's central venous system and/or heart, and producing heat exchange with a body fluid flowing through the patient's central venous system.

Cardiovascular guiding catheters are typically used in patients undergoing heart surgery to provide a path through a patient's vasculature through which other medical apparatus, such as other catheters or stent devices, may be advanced. Guiding catheters may also supply a conduit through which a contrast dye may be injected for diagnostic procedures, or through which other, smaller therapeutic catheters may be placed and maneuvered toward the patient's heart. Conventional cardiovascular guiding catheters are typically about 5 to 10 French in size and have a flexible single-lumen elongated body extending 80 to 110 centimeters. They typically may be introduced through the left or right coronary ostium, the subclavian or jugular veins, or through the femoral vein of the patient, serving to provide the caretaker with easy and convenient access to the patient's central blood supply via the central venous system. In this manner general access to the central blood supply is gained, enabling, for example, delivery of drugs, constrast dyes, fluids, along with the gathering of patient blood for blood gas analysis and the like.

One specific application for a guiding catheter is in balloon angioplasty procedures. Balloon angioplasty is a medical procedure used to widen narrowings in the coronary artery without surgery. The major challenge to angioplasty is clinical restenosis, or the re-narrowing of the blood vessel following the angioplasty procedure. Coronary stenting is a technique which mechanically props open the artery through implementation of a small, latticed stainless steel tube at the site of the narrowing. The stainless steel tube—the stent—is pre-mounted on a coronary angioplasty balloon catheter. As the balloon catheter is inflated during angioplasty, the stent expands and is compressed against the artery walls. When the balloon is deflated, the expanded stent remains implanted in the artery.

An introducer sheath may be inserted into a patient's vein to facilitate insertion of the guiding catheter. This sheath provides a direct and smooth pathway for the catheter to enter the artery. A coronary guiding catheter is inserted into the introducer sheath and may be advanced to the part of the aorta where the coronary arteries branch off to the heart. A hemostatic valve, which controls the flow of blood through the artery, is attached to the end of the coronary guiding catheter to allow for the insertion of coronary catheters. Note that a coronary guiding catheter is a conduit for the coronary guide wire and the coronary catheters to access the coronary artery. Coronary catheters rely on the support provided by the coronary guiding catheter.

A coronary guide wire is loaded into the coronary guiding catheter through the use of a guide wire introducer, and advanced to the cardiac vessel just past the narrowing. Coronary guide wires are used to support the coronary catheters as they are advanced across the artery narrowing. A torque device is placed on the end of the coronary guide wire and is used to steer the coronary guide wire to the artery until its tip is beyond the narrowing.

A coronary stent catheter is inserted at the distal end of the coronary guide wire and is advanced across the narrowing over the coronary guide wire through the guiding catheter.

After the plaque has been compressed and the artery has been opened sufficiently, the deflated coronary stent catheter may be withdrawn through the coronary guiding catheter, which itself is then removed.

In addition to using a guiding catheter to provide access to a patient's central venous system and/or heart, it may be desirable to reduce the patient's body temperature below normal body temperature so that the patient experiences hypothermia. Many advantages of hypothermia are known. By way of example, it has been found desirable to lower body temperature to reduce the metabolism of the body. This has been particularly desirable in surgical applications where the reduced metabolism has made it possible to more easily accommodate lengthy operative procedures. In cases of stroke and several other pathological conditions, hypothermia also reduces the permeability of the blood/brain barrier. It inhibits release of damaging neurotransmitters and also inhibits calcium-mediated effects. Hypothermia also inhibits brain edema and lowers intracranial pressure. In other cases, it may be desireable to cool a patient experiencing a fever so that the patient's body temperature returns to normal. Evidence suggests that cooling the body core is protective for the myocardium and the brain. Particularly, during accute myocardial infarction (AMI) and cardiac arrest (CA), the myocardium is deprived of adequate oxygen for extended periods of time and the brain is vulnerable to blood embolisms resulting from the impaired heart. These conditions can potentially be improved when the body is maintained at subnormal temperatures (32° C.–36° C.) during treatment. In treatment of myocardial infarction, angioplasty and stenting operations may also be included.

In yet other situations, it may be desirable to raise the patient's body temperature. Control of a patient's temperature may be problematic during hospital stays and particularly during active interventions such as surgery. The patient's body temperature may drift too low during surgery, potentially being deterimental to the patient's health. In such cases, body temperature may be artificially maintained at a normothermic temperature (approximately 98.6° F.). With regard to heart surgery, it may be particularly desireable to cool a patient before and/or during heart surgery and re-warm the patient post-operatively.

Conventional therapies used to manage patient temperature include acetaminophen (Tylenol), cooling blankets, heating blankets such as warm water blankets, forced warm or cool air, heat lamps, endovascular catheters, ice packs, ice baths, cold or warm infusions, and cold saline rectal or gastric ravages. With some of the conventional therapies, the warming or cooling rates are restricted by the body's ability to resist surface cooling or heating with vasodilation and sweating. The conventional approaches to cooling a patient also may require additional steps, may require excessive time and may not provide for precise control of patient temperature over long periods of time. Further, some of these devices cover a significant portion of a patient's body, inhibiting access to the patient.

Other techniques for controlling patient temperature employ intravascular heat exchange catheters that may be inserted into the patient's circulatory system. A relatively cool or warm fluid may be circulated through such catheters in a closed loop and exchange heat with blood flowing in the circulatory system, and may improve the patient's medical outcome.

Carrying out both the guiding function of a cardiovascular guiding catheter and the heat transfer function of a heat exchange catheter conventionally requires the use of two separate devices. Compared with using a single catheter, using both a heat exchange catheter and a cardiovascular guiding catheter would increase the complexity of the procedure, require addional steps to be carried out, and may require an additional incision.

In order to minimize the number of incisions and cardiovascular guiding catheter insertions into the patient's body and cool or heat the patient relatively quickly and in a controlled fashion, a cardiovascular guiding catheter may be configured to include a heat exchange capability.

By supplementing the known functions of a cardiovascular guiding catheter with the function of cooling or warming the patient's blood, a cardiovascular guiding catheter may take advantage of existing access to the venous system using a single, relatively small incision, reducing the risk of additional complications. One access is through the iliac arteries. Additional access may be through the subclavian, jugular or femoral veins to the central blood supply, via the central venous system, and is therefore particularly expedient, permitting efficient cooling or warming of a patient. The term central venous system generally relates to the portion of the venous system which returns blood to the right side of the heart, including the inferior and superior vena cava.

BRIEF SUMMARY OF THE INVENTION

It would be advantageous to provide a single cardiovascular guiding catheter that provides access to the patient's heart and bloodstream, facilitates guiding of other medical apparatus in the bloodstream, and provides intravascular cooling and heating, thereby overcoming one or more problems associated with the related art.

The present invention is directed to a heat exchange cardiovascular guiding catheter and methods for its use. A heat exchange element or elements is combined with a guide lumen and guide duct to provide efficient temperature control of a patient, to provide convenient access to the patient's heart and/or central venous system, and to provide a pathway through which medical apparatus may be advanced in the patient's bloodstream, all with a single catheter. Using a single catheter allows both the heat transfer function and the guiding function to be carried out simultaneously and reduces the complexity of providing the functions with two separate conventional devices.

In a first separate aspect of the invention, a heat exchange catheter comprises a guiding lumen and duct that facilitate insertion of medical apparatus in a patient's central venous system, and a heat exchange element that exchanges heat with the patient's blood so that a single cardiovascular guiding catheter carries out both the guiding function of a standard cardiovascular guiding catheter and the heat transfer function of a heat exchange catheter.

In a second separate aspect of the invention, a heat exchange cardiovascular guiding catheter comprises a generally tubular elongate body defining an inflow lumen, an outflow lumen, and at least one guide lumen. The inflow and outflow lumens supply heat exchange fluid to and from one or more heat exchange elements disposed about a distal, implantable portion of the catheter, while the guide lumen provides a pathway and access to the heart and/or central blood supply of the patient.

In a sixth separate aspect of the invention, a heat exchange cardiovascular guiding catheter is provided with multiple balloons (preferably three or four balloons) that are spaced along the elongated body to provide controlled and balanced heat transfer, with a gap between balloons to provide the catheter with flexibility.

In an eighth separate aspect of the present invention, it is contemplated that combinations of the foregoing separate aspects may be incorporated into a single embodiment.

Therefore, it is an object of the present invention to provide an improved heat exchange cardiovascular guiding catheter and a method for its use. Other and further objects and advantages will appear hereafter.

BRIEF DESCRIPTION OF THE DRAWINGS

FIG. 1 is a schematic side elevational view of a first embodiment of an intravenous cardiovascular guiding catheter;

FIG. 1A is a cross-sectional view of the intravenous cardiovascular guiding catheter of FIG. 1;

FIG. 2 is a schematic side sectional view of a distal portion of a second embodiment of an intravenous cardiovascular guiding catheter; and FIG. 3 is a schematic side sectional view of a distal portion of a third embodiment of an intravenous cardiovascular guiding catheter having a heating element.

DETAILED DESCRIPTION OF THE INVENTION

Figures 4, 5:
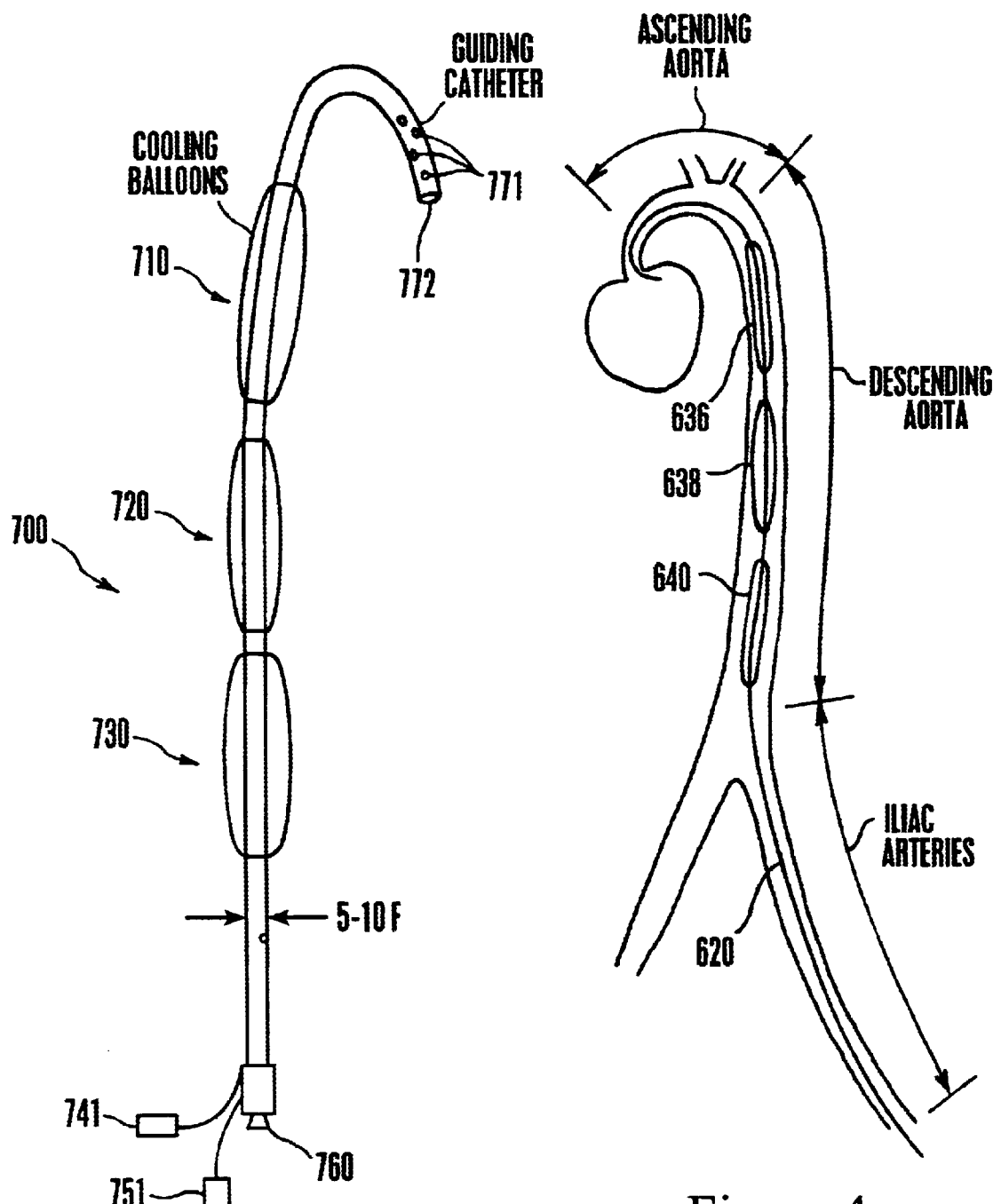
FIG. 4 shows an embodiment of a cardiovascular guiding catheter positioned in the ascending/descending aortic system.
FIG. 5 shows another embodiment of a cardiovascular guiding catheter.

The preferred embodiments will be described with reference to drawing figures, wherein like reference numerals are applied to like elements.

U.S. Pat. Nos. 6,146,411; 6,126,684; 6,299,599; 6,287,326; and 6,149,670 each of which is hereby incorporated by reference, disclose systems employing heat exchange catheters that may be inserted into the body of a patient to exchange heat with the blood supply of the patient. The indwelling catheters of the referenced patents are disposed in a heat exchange relationship with the blood supply, and a heat exchange fluid is circulated through the catheters in a closed loop. Outside the patient's body, the heat exchange fluid passes through a cooling or heating system to re-cool or re-heat the fluid. These catheters may change the patient's temperature and may thereby improve the patient's medical outcome.

The heat exchange capability and other advantages of the heat exchange catheters disclosed in the above-referenced patents may be implemented with a cardiovascular guiding catheter in the preferred embodiments here, so that a single device both accomplishes the functions of conventional guiding catheters and effectively manages patient temperature. By supplementing the known functions of a guiding catheter with the function of cooling or warming the patient's blood, a single heat exchange cardiovascular guiding catheter may be used to access to the venous system and cool or heat the patient through a single, relatively small incision, reducing the risk of complications. The access, typically through the femoral vein, is to the central blood supply, via the central venous system, and is therefore particularly expedient, permitting efficient cooling or warming of a patient. The term central venous system generally relates to the portion of the venous system which returns blood to the right side of the heart, including the inferior and superior vena cava.

FIGS. 1 and 1A depict one embodiment of a cardiovascular guiding catheter 20 adapted to exchange heat with a body fluid flowing through a body conduit of a patient, such as blood in a patient's central venous system. The catheter 20 comprises an elongate body 22 having a substantially tubular configuration, a proximal portion 26 with a proximal end 28, and a distal portion 30 with a distal end 31. When operatively disposed, the distal end 31 is disposed within the patient's body, and the proximal end 28 is disposed outside of the patient's body.

Referring also to FIG. 1A, which is a cross-sectional view taken along line 33 of the catheter 20 of FIG. 1, the elongate body 22 includes an inflow lumen 32, an outflow lumen 34, a guide lumen 44 and two auxiliary lumens 42, 46. The various lumens 32, 34, 42, 44, 46 extend between the proximal portion 26 and the distal portion 30 of the elongate body 22. External access to the inflow lumen 32 and outflow lumen 34 is provided by an inlet tube 52a and an outlet tube 52b. External access to the guide lumen 44 and two auxiliary lumens 42, 46 is supplied by a guide lumen fitting 74 through which medical apparatus could be introduced, and auxiliary lumen fittings 76, 78.

The elongate body 22 preferably includes a reinforcing member that prevents the catheter from kinking when it flexes and may provide torsional stiffness for torqueability. In this embodiment, the reinforcing member 25 comprises a wire embedded in and wound inside the material 23 of the elongate body in a series of turns. The part of the reinforcing member 25 indicated with a solid line is that portion which may be visible at the cross-section shown. Preferably, the member 25 is wound through at least a substantial portion of the distal portion 30 of the catheter 20 because the distal portion 30 may be subjected to forces that might cause the catheter to kink in the absence of the member 25. The reinforcing member 25, however, does not extend to the distal end 31 of the elongate body 22 because the portion of the elongate body 22 adjacent the distal end 31 preferably is flexible for maneuverability through the patient's vasculature. A reinforcing member may comprise any type of structure that inhibits kinking of the catheter 20, such as wire braiding in the elongate body or one or more longitudinal slats embedded in the elongate body 22 or in one of the lumens 32, 34, 42, 44, 46.

In this embodiment, the elongate body 22 has a guide duct 70 at the distal end 31 of the elongate body 22 for providing communication between the guide lumen 44 and the patient's body conduit in which the catheter 20 may be inserted. Other guide ducts 71 may be disposed about a longitudinal side of the elongate body 22 near the distal end 31. A catheter may include any or all of the guide ducts 70, 71 shown, and may include additional guide ducts not shown.

Preferably, the guide lumen 44 or the guide lumen fitting 74 has a barrier 77 located proximally of the proximal-most guide duct 70, 71 to selectively block and/or restrict fluid flow through the lumen 44 or fitting 74. Such a barrier 77 may comprise a valve, such as a hemostasis valve, a plug or any other means for selectively blocking the guide lumen 44 or guide lumen fitting 74.

At least one heat exchange element 24, such as a fluid-carrying inflatable balloon, preferably is disposed proximally of at least one of the guide ducts 70, 71 and extends at least partially along the implantable, distal portion 30 of the elongate body 22. For illustrative purposes, this embodiment is shown to have only one heat exchange element 24. Preferably, however, a catheter has more than one heat exchange element (as will be described below in connection with other embodiments), and may have numerous heat exchange elements.

Heat exchange fluid (not shown) flows through the elongate body and through the heat exchange element 24 to heat or cool a patient. The heat exchange fluid is supplied through the inflow lumen 32 and enters the heat exchange element 24 through an inflow duct 50, then flows through the heat exchange element 24, and exits through an outflow duct 61. The heat exchange fluid is remotely cooled or heated outside of the catheter 20, such as by a temperature control system (not shown), as described in U.S. Pat. Nos. 6,146,411 and 6,019,783, both of which are incorporated by reference herein, and is conveyed to and from the catheter 20 via the inlet tube 52a and the outlet tube 52b.

The particular heat exchange fluid selected is preferably biocompatible to avoid harm to the patient in the event of inadvertent rupture. Candidate materials include sterile saline and water, although other fluids having suitable viscosity, heat exchange and material compatibility characteristics can also be used.

The auxiliary lumens 42, 46 may serve one or more of a variety of functions, including providing a conduit for infusion of drugs such as chemotherapy, fluids and nutrition, providing access for syringes for sampling, and accommodating various sensors, such as a blood pressure sensors and thermistors to monitor the patient, thus generally providing access to the central blood supply as dictated by the particular application. The auxiliary lumens 42, 46 each preferably have an auxiliary duct 75, 72, 71 that provides fluid communication between each auxiliary lumen 42, 46 and the outside surface of the catheter 20 so that the auxiliary lumens 42, 46 provide access to the body conduit in which the catheter 20 is inserted. Although one auxiliary duct 75 is shown proximal of the heat exchange element 24 on the hidden side of the elongate body 22 (as indicated by dashed lines) and the other auxiliary duct 71, 72 is shown distal of the heat exchange element 24, the auxiliary ducts 75, 72, 71 alternately may be disposed at other locations on the the catheter 20. Further, the auxiliary lumens 42, 46 may be configured to receive a guidewire, which may be used to stiffen the catheter 20 during insertion and removed after insertion, or the guide lumen 44 may accommodate a guidewire. While the catheter 20 depicted in FIG. 1 has two auxiliary lumens 42, 46, other numbers of auxiliary lumens are contemplated and may be suitable depending on the particular application.

The guide lumen 44 preferably occupies a subtantial portion of the cross-sectional area of the elongate body 20 to provide adequate space for the insertion of medical apparatus. The various lumens 32, 34, 42, 44, 46, however, may have cross-sectional shapes and sizes different that those depicted in FIG. 1A as suitable for the particular application.

The catheter 20 preferably is formed of a polymer material 23 that defines the various lumens 32, 34, 42, 44, 46. A preferred material 23 is polyurethane, although other materials, such as nylon, polyethylene, PEBAX, PVC, Tygon® or the like may also be used. Considerations in selecting the appropriate material 23 include biocompatibility, flexibility, temperature change compatibility, and resistance to buckling.

As shown in FIG. 1, one or more depth markings 60, 62 may be disposed on the elongate body 22 to indicate the length of a portion of the catheter 20 that is inserted into the patient. Preferably, the depth markings 60, 62 are disposed at least on the proximal portion 26 of the elongate body 22 so that they are visible when the catheter 20 is inserted into the patient. The markings 60, 62 may indicate a length of the catheter 20 measured from each marking 60, 62 to the distal end 31 of the catheter 20, and may be disposed at spaced intervals, such as one-centimeter intervals. Each marking 60, 62 may comprise any symbol that may be understood to represent a length or relative length or degree of intubation. One marking 60 is shown to comprise a numeral indicative of length (in centimeters, for example) from the marking 60 to the distal end 31 of the catheter. Other markings 62 may comprise dots, lines, hash marks or other marks.

The elongate body 22 may also include a distal indicator 64 that indicates the position of the distal end 31 of the elongate body 22. The distal indicator 64 preferably is disposed near the distal end 31 of the elongate body 22. The position of the distal indicator 64 inside the patient preferably may be determined using conventional medical technology, such as X-ray technology or fluoroscopy. Information regarding the position of the distal end 31 of the elongate body 22 may aid proper placement of the catheter 20, so that the catheter 20 is inserted to a degree that maximizes the heat transfer rate without harming the patient.

The catheter 20 preferably includes an anchor configured for affixing the catheter 20 to the patient. As shown in FIG. 1, the anchor may comprise a suture fitting 80. The suture fitting 80 can be made integrally with the catheter 20, or it can be made as a separate plastic fitting and engaged with the catheter 20. The suture fitting 80 includes two eyes 82, 84 through which sutures can be inserted and engaged with the patient or with a bandage or tape or other structure that is engaged with the patient. An anchor may be especially desirable in cases in which the catheter is inserted for an extended period.

The implanted portion of the catheter 20 may also be thromboresistant. The thromboresistant property may be provided, for example, in the form of a coating having thromboresistant characteristics. The coating may include an anticoagulant and/or be adapted to receive an electrical charge providing thromboresistance to the coating. Further, a hydrophilic coating may be applied to the catheter to discourage the adhesion of body fluids or tissue to the catheter.

Although FIG. 1 depicts a catheter with a single heat exchange element, a cardiovascular guiding catheter may be provided with various numbers of heat exchange elements. FIG. 2 depicts a cross-section of a distal portion of a catheter 120 having three heat exchange elements 124, 126, 128. The principles described herein typically apply to catheters having any number of heat exchange elements.

The three heat exchange elements 124, 126, 128 are disposed proximally of the guide ducts 170, 171a, 171b. Each heat exchange element 124, 126, 128 preferably comprises a balloon that is inflatable from a deflated configuration, wherein the balloon lies substantially flush with the elongate body 122, to an operational configuration wherein the balloon is expanded away from the elongate body 122 by the pressure of the heat exchange fluid inside the balloon. The deflated configuration facilitates insertion and removal of the catheter 120, and the inflated configuration provides greater heat transfer capability.

Each heat exchange element 124, 126, 128 defines with the elongate body 122 a cavity 136, 138, 140. Heat exchange fluid (as indicated by the arrows) is circulated through the heat exchange elements 124, 126, 128 via the inflow lumen 132 and the outflow lumen 134. Heat exchange fluid introduced into the inflow lumen 132 flows through each inflow duct 150, 152, 154 and enters each cavity 136, 138, 140 of each heat exchange element 124, 126, 128. The heat exchange fluid flows through each heat exchange element 124, 126, 128 and exits each heat exchange element 124, 126, 128 through each outflow duct 160, 162, 164. The heat exchange fluid then flows through the outflow lumen 134 toward the proximal end of the catheter 120. The elongate body 122 may also define auxiliary lumens like those described in connection with FIGS. 1 and 1A.

The inflow duct 150, 152, 154 of each heat exchange element 124, 126, 128 preferably is positioned distally of the corresponding outflow duct 160, 162, 164 to provide countercurrent flow, which facilitates the maximum heat exchange between the heat exchange fluid and the body fluid (e.g., blood). Further information regarding the structure, functions, positions and relative sizes of inflow ducts and outflow ducts is disclosed in U.S. Pat. No. 6,126,684.

The heat exchange fluid may be either relatively cool or relatively warm, depending on whether patient cooling or heating is desired. While in each cavity 136, 138, 140, the heat exchange fluid serves to provide a cold or warm fluid on an inner surface of each heat exchange element 124, 126, 128. With a body fluid, such as blood, flowing exteriorly of each heat exchange element 124, 126, 128, heat transfer occurs across each heat exchange element 124, 126, 128, effectively cooling or heating the body of the patient. The temperature of the heat exchange fluid is remotely controlled in order to achieve a desired patient target temperature or temperature range.

Each heat exchange element 124, 126, 128 preferably comprises a balloon. Each balloon may be formed from a piece of flexible sheet material or extruded tubing formed into a molded balloon of the desired shape and size and then bound or otherwise fixed to the elongate body 122 to form each cavity 136, 138, 140. In one embodiment, each heat exchange element 124, 126, 128 is made of urethane, nylon, or PET and is thin-walled, i.e., has a wall thickness of less than three mils, and more preferably less than one and one-half mils. Further, each heat exchange element 124, 126, 128 preferably is coated with an antimicrobial substance, as well as an anticlot substance, such as heparin.

One advantage of using multiple heat exchange elements 124, 126, 128 is that the flow and temperature of heat exchange fluid may be more readily controlled along the catheter 120 such that a more even and balanced transfer of heat can be achieved. Further, multiple heat exchange elements 124, 126, 128 may provide an increased surface area relative to embodiments having a single heat exchange element. Another advantage of using multiple heat exchange elements 124, 126, 128 is the ability of the catheter 120 to bend and flex when placed in a curved vasculature.

In preparation for withdrawing the catheter 220 from the patient, each heat exchange element 224, 226, 228 preferably is deflated to facilitate withdrawal and avoid damaging the heat exchange elements 224, 226, 228 or the patient's vasculature during withdrawal. The heat exchange elements 224, 226, 228 may be deflated by allowing heat exchange fluid to drain out of each heat exchange element 224, 226, 228. Pressure in the inflow lumen 232 and/or outflow lumen 234 may be decreased to help draw the heat exchange elements 224, 226, 228 toward the elongate body 222, such as by applying suction to both the inflow lumen 232 and the outflow lumen 234 or applying suction to either lumen 232, 236 and blocking the other lumen 236, 232.

A cardiovascular guiding catheter preferably has a size (e.g., length and cross-sectional area) that maximizes the heat transfer rate without causing harmful physiological effects. It is believed that in at least some blood vessels, flow of blood through the vessel begins to be reduced when approximately 50% of the blood vessel cross section is blocked. To maintain blood flow, the cross-sectional size (e.g., diameter and/or area) of the catheter preferably is no more than approximately 30% to 75% of the cross-sectional size of the blood vessel in which the balloon is inserted, which will vary with the size of each patient's vasculature. This range may be modified to provide a suitable safety margin.

Various balloon configurations for the heat exchange elements may be employed, including but not limited to straight, helical, cylindrical, and fluted shapes. U.S. patent application Ser. No. 10/015,505, which describes heat exchange elements of various shapes, is hereby incorporated by reference. The particular configuration selected depends on the application and the desired heat exchange and other characteristics. Preferably, each heat exchange element has a configuration that safely maximizes the rate of heat transfer. The rate of heat transfer depends on many factors, such as the volumetric flow rates of the blood and the heat exchange fluid, the temperature difference between the heat exchange element and the blood, the thermal conductivity and thickness of the barrier between the two fluids, and the residence time of the heat transfer.

The rate of heat transfer may also depend partially on the geometry of the heat exchange element. Heat exchange may be enhanced when the heat exchange fluid is provided with well mixed flow. Mixing can be enhanced by providing an irregular surface next to which the heat exchange fluid flows, such as an irregular inner balloon surface or obstructions inside the heat exchange element. The configuration of the balloon itself, such as a spiral-shaped balloon, also may encourage mixing.

Although a heat exchange element may comprise a balloon, a heat exchange element alternately may have a different configuration, such as an array of flexible hollow fibers through which the heat exchange fluid is circulated. Further information regarding hollow fiber heat exchange elements and catheter systems having hollow fibers is disclosed in U.S. Pat. No. 6,165,207, which is hereby incorporated by reference as if fully set forth herein.

In some embodiments, a heat exchange fluid is heated or cooled outside of the catheter and circulates through one or more heat exchange elements. As shown in FIG. 3, however, instead of circulating substantially continuously through each heat exchange element 624, 626, 628, the heat exchange fluid alternately may enter each heat exchange element 624, 626, 628 and remain in each heat exchange element 624, 626, 628 while being heated or cooled by a heating element 610. The heating element 610 may include a wire or other conductive material, a refrigerant, or other material that may be used to heat or cool the heat exchange fluid.

The heating element 610 preferably is disposed near the heat exchange elements 624, 626, 628 so that the heating element 610 may efficiently exchange heat with the heat exchange fluid inside the cavities 636, 638, 640 of the heat exchange elements 624, 626, 628. Preferably, the heating element 610 is embedded in or disposed along or near at least part of the distal portion of the elongate body 622.

A heat source (not shown) is used to heat or cool the heating element 610. The heat source preferably is located externally of the catheter 620 and is electrically, thermally or otherwise coupled with the heating element 610. The heat source may include an electrical source, a heater, a refrigerator, a laser, a radio frequency (RF) energy source, a microwave energy source, an ultrasonic energy source, or other source of heat transfer.

Because the heat exchange fluid is not continuously circulating through the heat exchange elements 624, 626, 628, separate inflow and outflow lumens are not needed. Instead, a single flow lumen 632 may be employed to deliver heat exchange fluid through flow ducts 650, 652, 654 both to and from the cavities 636, 638, 640 of the heat exchange elements 624, 626, 628. A pump or gravity may be used to move heat exchange fluid into the heat exchange elements 624, 626, 628. A pump, suction or gravity may be used to move heat exchange fluid out of the heat exchange elements 624, 626, 628. The structure and function of the flow lumen 632 and flow ducts 650, 652, 654 are similar to that of the inflow lumens and ducts and outflow lumens and ducts described in connection with other embodiments, except that the flow lumen 632 and flow ducts 650, 652, 654 are used to transport heat exchange fluid both to and from the heat exchange elements 624, 626, 628. A body fluid is diverted from the patient's body conduit through guide ducts 670, 671*a*, 671*b* disposed near a distal end 631 of the catheter 620 and into the guide lumen 641

An infusion lumen 634 extends through the elongate body 622 and may communicate with the patient's body conduit through each of various infusion ducts 685, 687, 689 disposed on the elongate body 622. The infusion ducts 685, 687, 689 preferably are disposed adjacent to or between heat exchange elements 624, 626, 628.

Alternately, the catheter 620 may have three separate infusion lumens, each communicating with a single infusion duct 685, 687, 689. Providing multiple infusion lumens with infusion ducts that are spaced apart on a catheter allows, for example, the simultaneously delivery different medications to the patient at different locations in the patient's bloodstream, which may be especially desirable where mixing of the medications in relatively high concentrations is desired to be avoided.

In catheters having multiple heat exchange elements, the heat exchange elements are preferably spaced apart to define one or more gaps where the elongate body is exposed. Infusion ducts and guide ducts may be located in gaps between heat exchange elements, and/or also may be located adjacent to a single heat exchange element, such as proximal of a proximal-most balloon. An infusion duct or guide duct may also be disposed at or near a distal tip of the catheter. Additionally, guide ducts and auxiliary ducts such as infusion ducts may be provided at any combination of various locations.

Alternately, the catheter 620 of FIG. 3 may be configured without a heating element 610. In such an embodiment (not shown), the heat exchange fluid may be heated or cooled outside of the catheter and pumped into one or more heat exchange elements. The heat exchange fluid may remain in the heat exchange element, exchanging heat with the patient's tissue for some time (e.g., until the heat exchange fluid and adjacent tissue are nearly the same temperature), and then be removed from the heat exchange element. This process may then be repeated any number of times, the heat exchange fluid being re-heated or re-cooled outside of the catheter, and pumped back into the heat exchange element(s) to transfer heat with the patient's blood.

The guiding catheter 700 of FIG. 5 includes three heat exchange cavities 710, 720, 730. Heat exchange fluid is circulated through these cavities 710, 720, 730 via an inflow lumen 740 (not shown) and an outflow lumen 750 (not shown). The heat exchange fluid flows from the fluid source (not shown) to the inflow duct 741 to reach the inflow lumen 740, and then flows through the cavities 710, 720, 730 out to the outflow lumen 750 to reach the outflow duct 751 and back to the fluid source. Additionally, the guiding catheter 700 includes a guide lumen 761 (not shown) which is connected to the guide duct 760 at its proximal end. Several auxiliary ducts 771, 772 are found on the distal end of the guiding catheter. These auxiliary ducts are connected to the guide lumen 761 and are configured to receive a guidewire. In the alternative, the auxiliary ducts may be used as infusion ports for medication or nutrients into the patient's body. Typically, the guiding catheter 700 measures about 5 to 10 French in size and has a flexible elongated body extending 80 to 110 cm in length.

In accordance with a preferred method of use, the catheter may be inserted percutaneously through a puncture or surgical cut near the groin. Prior to insertion, the size (e.g., cross-sectional size and/or length) of the body conduit in which the catheter is to be inserted may be measured, and a catheter may be selected based on the size of the body conduit, so that the catheter maximizes the heat transfer rate without deleterious physiological effects on the patient.

Preferably, the catheter is inserted into the patient with each heat exchange element being deflated and lying substantially flush with the elongate body. This configuration facilitates insertion of the catheter and avoids damaging the catheter or harming the patient during insertion.

Following this initial introduction, the catheter may be moved through the iliac arteries, and into the descending aorta of a patient as shown in FIG. 4. Typically, the distal end of a cardiovascular guiding catheter is positioned in the ascending aorta, while the heat exchange portion of the catheter is positioned in the descending aotria.

Once inserted in the patient, a cardiovascular guiding catheter may be used to provide general access to the central blood supply and guide medical apparatus in the patient's circulatory system, enabling heat transfer, delivery of drugs, infusion fluids or nutrition, along with the introduction of medical apparatus.

Each heat exchange element may be inflated with heat exchange fluid that is circulated through each heat exchange element to exchange heat with the patient's blood. The heat exchange relationship between the catheter and the circulatory system of the patient may be maintained for a prolonged duration—for example, from about one hour to about twenty-nine days.

To facilitate removal of the catheter from the patient, each heat exchange element preferably is deflated by removing heat exchange fluid from each heat exchange element. Suctions may be applied to the inflow lumen and/or outflow lumen to facilitate removal of heat exchange fluid.

The catheter systems disclosed herein may be used in connection with systems for treating cardiac arrest that are disclosed in U.S. Pat. No. 6,149,670, which is hereby incorporated by reference as if fully set forth herein.

While the present invention has been described in terms of the preferred embodiments, other variations which are within the scope of the invention as defined in the claims will be apparent to those skilled in the art.

What is claimed is:

1. A cardiovascular guiding catheter adapted to exchange heat with a body fluid in a body conduit of a patient; the cardiovascular guiding catheter comprising:
    an elongate body including an inflow lumen, an outflow lumen and a guide lumen each extending through the elongate body;
    at least one guide duct disposed near a distal end of the elongate body and in fluid communication with the guide lumen;
    a first heat exchange element in which a heat exchange fluid may flow, the first heat exchange element being in fluid communication with the inflow lumen and the outflow lumen; and
    a second heat exchange element disposed proximally to the first heat exchange element and movable between a deflated configuration substantially flush with the elongate body and an inflated configuration in which the second heat exchange element is inflated outwardly from the elongate body by the heat exchange fluid.

2. The cardiovascular guiding catheter of claim 1, the first heat exchange element being disposed proximally to the guide duct and movable between a deflated configuration substantially flush with the elongate body and an inflated configuration in which the first heat exchange element is inflated outwardly from the elongate body by the heat exchange fluid.

3. The cardiovascular guiding catheter of claim 1, the first heat exchange element having a diameter of approximately 3 mm to approximately 12 mm, and the second heat exchange element having a diameter of approximately 3 mm to approximately 12 mm.

4. The cardiovascular guiding catheter of claim 1, the elongate body including a reinforcing member.

5. The cardiovascular guiding catheter of claim 4, the reinforcing member including a wire embedded in and wound in the elongate body in a series of turns.

6. The cardiovascular guiding catheter of claim 1, the catheter further comprising
    one or more of a group comprising a temperature sensor and a blood pressure sensor.

7. The cardiovascular guiding catheter of claim 1, the elongate body having a diameter of about 5 French to approximately 24 French.

8. A cardiovascular guiding catheter adapted to exchange heat with a body fluid in a body conduit of a patient, the cardiovascular guiding catheter comprising:
    an elongate body including an inflow lumen, an outflow lumen and a guide lumen each extending through the elongate body;

at least one guide duct disposed near a distal end of the elongate body and in fluid communication with the guide lumen;

a first heat exchange element in which a heat exchange fluid may flow, the first heat exchange element being in fluid communication with the inflow lumen and the outflow lumen; and the elongate body, further including an infusion lumen extending therethrough.

9. A cardiovascular guiding catheter adapted to exchange heat with a body fluid in a body conduit of a patient, the cardiovascular guiding catheter comprising:

an elongate body including an inflow lumen, an outflow lumen and a guide lumen each extending through the elongate body;

at least one guide duct disposed near a distal end of the elongate body and in fluid communication with the guide lumen;

a first heat exchange element in which a heat exchange fluid may flow, the first heat exchange element being in fluid communication with the inflow lumen and the outflow lumen; and the elongate body further including one or more of a group comprising a barrier, a valve and a plug for selectively blocking the guide lumen or a guide lumen fitting.

10. A cardiovascular guiding catheter adapted to exchange heat with a body fluid in a body conduit of a patient, the cardiovascular guiding catheter comprising:

an elongate body including an inflow lumen, an outflow lumen and a guide lumen each extending through the elongate body;

at least one guide duct disposed near a distal end of the elongate body and in fluid communication with the guide lumen;

a first heat exchange element in which a heat exchange fluid may flow, the first heat exchange communication element being in fluid with the inflow lumen and the outflow lumen; and the catheter further comprising:
a heating element for transferring heat with the heat exchange element; and
a heat source for heating or cooling the heating element.

11. A cardiovascular guiding catheter of claim 10, the heat source including one or more of a group including an electrical source, a heater, a refrigerator, an air compressor, a laser, an RF energy source, a microwave energy source, and an ultrasonic energy source.

12. A cardiovascular guiding catheter adapted to exchange heat with a body fluid in a body conduit of a patient, the cardiovascular guiding catheter comprising:

an elongate body including inflow means for conveying a heat exchange fluid toward a distal portion of the elongate body, outflow means for conveying the heat exchange fluid toward a proximal portion of the elongate body, and guide means for guiding a medical instrument in the body conduit; and heat exchange means for exchanging heat between the heat exchange fluid and the body fluid in the patient's body conduit, the heat exchange means being in fluid communication with the inflow means and the outflow means, the elongate body further including barrier means for selectively blocking the guide means.

13. The cardiovascular guiding catheter of claim 12, the elongate body further including infusion means for in sing an infusion fluid into the patient's body conduit.

14. A cardiovascular guiding catheter adapted to exchange heat with a body fluid in a body conduit of a patient, the cardiovascular guiding catheter comprising:

an elongate body including inflow means for conveying a heat exchange fluid toward a distal portion of the elongate body, outflow means for conveying the heat exchange fluid toward a proximal portion of the elongate body, and guide means for guiding a medical instrument in the body conduit; and heat exchange means for exchanging heat between the heat exchange fluid and the body fluid in the patient's body conduit, the heat exchange means being in fluid communication with the inflow means and the outflow means, the catheter further comprising:
heating means for transferring heat with the heat exchange means; and
heat source means for hating or cooling the heating means.

15. A method for controlling a temperature of a patient and guiding a medical instrument in a body cavity of the patient, comprising the steps of:

providing a cardiovascular guiding catheter comprising an elongate body, at least one heat exchange element, at least one guide lumen, and at least one guide duct;

placing the at least one eat exchange element in a heat exchange relationship with the body fluid in the body conduit;

providing heat transfer with the heat exchange element such that the heat exchange element is heated or cooled;

placing the at least one guide duct in the body conduit; and guiding a medical instrument in the body cavity through the guide duct and guide lumen.

16. The method of claim 15, the step of providing heat transfer with the at least one heat exchange element including the step of circulating a heat exchange fluid through the at least one heat exchange element to effect heat transfer with the body fluid in the body conduit.

17. The method of claim 15, the catheter further comprising at least one infusion lumen, the method further comprising the step of infusing a fluid into the body conduit via the at least one infusion lumen.

18. A method as set forth in claim 17, the step of guiding a medical instrument in the body cavity including the step of advancing the medical instrument through the guide lumen and guide duct.

19. A method as set forth in claim 15, the step of providing heat transfer with the heat exchange element including the step of expanding the heat exchange element with a heat exchange fluid.

20. A method as set forth in claim 15, the step of providing heat transfer with the heat exchange element including the step of changing a temperature of the heat exchange fluid with electric resistive heating, a laser, RF energy, microwave energy, ultrasonic energy or a heat sink.

21. A method of reducing myocardial infarction by intravascular application of hypothermia, the method comprising the steps of:

inserting a guiding catheter into the vasculature of a patient, the guiding catheter adapted to exchange heat with a body fluid in a body conduit of a patient and the guiding catheter comprising:

an elongate body including an inflow lumen, an outflow lumen and a guide lumen each extending rough the elongate body;

at least one guide duct disposed near a distal end of the elongate body and in fluid communication with the guide lumen; and a first heat exchange element in which a heat exchange fluid may flow, the first heat exchange element being in fluid communication with the inflow lumen and the outflow lumen;

maintaining heat exchange with the patient's body fluid for a sufficient length of time to reach a predetermined temperature threshold.

22. The method of claim 21 wherein the body fluid is the paient's blood.

23. The method of claim 21 further comprises the step of circulating cooling fluid from an external source to and from the first heat exchange element.

24. The method of claim 21 wherein the guiding catheter further comprises a second heat exchange element in which the heat exchange fluid may flow, the second heat exchange element being in fluid communication with the inflow lumen and the outflow lumen.

25. The method of claim 21 further comprises the step of angioplasty or stenting operation on a blood vessel of the patient.

* * * * *